(12) United States Patent
Drent et al.

(10) Patent No.: US 7,858,787 B2
(45) Date of Patent: Dec. 28, 2010

(54) PROCESS FOR PRODUCING OLEFINS

(75) Inventors: Eit Drent, Amsterdam (NL); Roelof Van Ginkel, Amsterdam (NL); Willem Wabe Jager, Amsterdam (NL)

(73) Assignee: Shell Oil Company, Houston, TX (US)

( * ) Notice: Subject to any disclaimer, the term of this patent is extended or adjusted under 35 U.S.C. 154(b) by 601 days.

(21) Appl. No.: 11/857,011

(22) Filed: Sep. 18, 2007

(65) Prior Publication Data

US 2008/0081909 A1 Apr. 3, 2008

(30) Foreign Application Priority Data

Sep. 22, 2006 (EP) ................................. 06254916

(51) Int. Cl.
*C07F 9/02* (2006.01)
*C07C 233/00* (2006.01)
*C07C 45/00* (2006.01)
*C07C 5/00* (2006.01)

(52) U.S. Cl. .................. 544/337; 564/123; 568/12; 568/426; 568/429; 568/454; 568/455; 568/456; 585/250

(58) Field of Classification Search ................ 585/640, 585/250; 568/8, 12, 909, 426, 429, 454, 568/455, 456; 564/123; 544/337
See application file for complete search history.

(56) References Cited

U.S. PATENT DOCUMENTS

| | | | | |
|---|---|---|---|---|
| 3,440,291 | A | 4/1969 | Van Winkle et al. | 260/632 |
| 3,448,157 | A | 6/1969 | Slaugh et al. | 260/604 |
| 3,501,515 | A | 3/1970 | Van Winkle et al. | 260/439 |
| 3,959,386 | A | 5/1976 | Pinke | 260/604 HF |
| 4,210,608 | A | 7/1980 | Pinke | 568/451 |
| 4,777,320 | A | 10/1988 | Alvila et al. | 585/139 |
| 5,057,638 | A | 10/1991 | Sweeney | 585/324 |
| 5,488,174 | A | 1/1996 | Drent et al. | 568/454 |
| 5,985,238 | A | 11/1999 | Pasquale et al. | 423/706 |
| 6,037,506 | A | 3/2000 | Bolinger | 568/909 |
| 6,156,936 | A | 12/2000 | Drent et al. | 568/454 |
| 6,627,782 | B2 | 9/2003 | Kaizik et al. | 585/639 |
| 2005/0065389 | A1 | 3/2005 | De Bruyn et al. | 585/639 |

FOREIGN PATENT DOCUMENTS

| | | |
|---|---|---|
| EP | 0424767 | 10/1990 |
| GB | 797989 | 7/1958 |
| JP | 3141234 | 3/2001 |
| WO | WO 03024910 | 3/2003 |
| WO | WO 2005058788 | 6/2005 |

OTHER PUBLICATIONS

Office Communication for U.S. Appl. No. 10/489,216, filed Nov. 1, 2004.
M.R. Eberhand, E. Carrington-Smith, E. Drent, P.S. Marsh, A.G. Orpen, H. Phetmung and P.G Pringle, Adv. Synth. Catal, 2005, 347, 1345.
J.H. Downing, V. Gee and P.G. Pringle, Chem Commun., 1997, 1527.
Keulemans, A.I.M. et al., "The Structure of teh Formylation (OXO) Products Obtained from Olefines and Watergas," RECL. TRAV. CHIM. PAYS-BAS, vol. 67, pp. 298-308, (1948).
Kim B. et al., "Polystyryltri-*n*-butylphosphine," J. Org. Chem., vol. 49, No. 17, pp. 3233-3235 (1984).

*Primary Examiner*—Prem C Singh
*Assistant Examiner*—In Suk Bullock

(57) ABSTRACT

A process for converting an olefin having x carbon atoms into an olefin having x+1 carbon atoms wherein the process comprises the steps of:
  (i) reacting an olefin having x carbon atoms with carbon monoxide and hydrogen in the presence of a hydroformylation catalyst to produce an alcohol having x+1 carbon atoms, and
  (ii) dehydrating the alcohol produced in step (i) in the presence of a dehydration catalyst to produce an olefin having x+1 carbon atoms characterized in that the hydroformylation catalyst used in step (i) is based on:
  (a) a source of cobalt, and
  (b) a ligand which contains phosphorus and nitrogen.

10 Claims, No Drawings

PROCESS FOR PRODUCING OLEFINS

FIELD OF THE INVENTION

The present invention relates to a process of producing olefins, in particular to a process for converting an olefin having x carbon atoms into an olefin having x+1 carbon atoms.

BACKGROUND OF THE INVENTION

There is a high demand for longer chain α-olefins, especially even numbered α-olefins such as 1-hexene and 1-octene. 1-hexene and 1-octene are used, amongst others, as co-monomers in polyethylene production where they serve as plasticizers e.g. in the preparation of linear low density-polyethylene.

One method of producing olefins is through an olefin metathesis reaction. A disadvantage of this type of reaction is that it is difficult to control the reaction to produce only one specific olefin, and the majority of olefins produced by this process are internal olefins. Metathesis reactions are accordingly not very suitable for preparing α-olefins such as 1-hexene or 1-octene. One type of metathesis reaction, namely ethenolysis between an internal olefin and ethylene, can potentially yield α-olefins, but the technology suffers from equilibrium and selectivity limitations. Furthermore, ethenolysis of an internal olefin would result in an olefin with a shorter chain than the starting internal olefin.

1-Hexene can also be produced by the trimerisation of ethylene, however C4, C8 and C10 impurities are also produced.

WO03/024910 discloses a process of increasing the carbon chain length of olefinic compounds, including α-olefins, such that 1-pentene can be converted to 1-hexene and 1-heptene can be converted to 1-octene. The process comprises the steps of:— provide a starting olefinic compound and subjecting it to hydroformylation to produce an aldehyde and/or alcohol with an increased carbon chain length compared to the starting olefinic compound;

optionally, hydrogenating the aldehyde that forms during the hydroformylation reaction to convert it to an alcohol which has an increased carbon chain length compared to the starting olefinic compound; and subjecting the alcohol with the increased carbon chain length to dehydration to produce an olefinic compound with an increased carbon chain length compared to the starting olefinic compound.

Although α-olefins such as 1-hexene and 1-octene can be produced by the process of WO03/024910, the process suffers from several disadvantages. Firstly, as can be seen from the Examples in WO03/024910, the alcohols formed during the hydroformylation step have a relatively low linearity (i.e. not more than about 88%). Low linearity in the alcohols formed during the hydroformylation step renders the process undesirable from an economical point of view. Further, in the process of WO03/024910 it is desirable to remove branched alcohols from the hydroformylation product before dehydration in order to achieve an acceptable purity of the final α-olefin product.

It would therefore be desirable to provide a process for producing α-olefins which obviates the above disadvantages.

It has now been found by the present inventors that by using a specially selected hydroformylation catalyst the linearity of the alcohol produced in the hydroformylation step can be improved. In addition, the use of the specially selected hydroformylation catalyst leads to an overall improvement in the purity of the final α-olefin product.

SUMMARY OF THE INVENTION

According to one aspect of the present invention there is provided a process for converting an olefin having x carbon atoms into an olefin having x+1 carbon atoms wherein the process comprises the steps of:

(i) reacting an olefin having x carbon atoms with carbon monoxide and hydrogen in the presence of a hydroformylation catalyst to produce an alcohol having x+1 carbon atoms, and (ii) dehydrating the alcohol produced in step (i) in the presence of a dehydration catalyst to produce an olefin having x+1 carbon atoms characterised in that the hydroformylation catalyst used in step (i) is based on:

(a) a source of cobalt, and (b) a ligand selected from:
  (i) a ligand of general formula (I):

wherein $R^1$ and $R^2$ are independently a hydrocarbyl group with $C_1$-$C_{12}$ carbon atoms or together with the phosphorus atom P represent an optionally substituted cyclic group with at least 5 ring atoms; and wherein $R^3$ is a monovalent radical of general formula:

wherein $R^4$ is an alkylene group and $R^5$ and $R^6$ independently represent an alkyl, cycloalkyl, aryl, alkaryl or heteroaryl group;

(ii) a ligand of general formula (III):

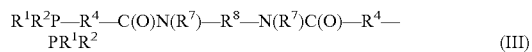

wherein $R^1$, $R^2$ and $R^4$ are as defined above, wherein $R^7$ independently represents an alkyl, cycloalkyl, aryl, alkaryl or heteroaryl group, and wherein $R^8$ represents an alkylene, cycloalkylene, arylene or alkarylene group; and (iii) a ligand of general formula (IV):

wherein $R^1$, $R^2$, $R^4$ and $R^8$ are as defined above; and mixtures thereof.

DETAILED DESCRIPTION OF THE INVENTION

In the first step of the process an olefin having x carbon atoms is subjected to a hydroformylation reaction by reacting with carbon monoxide and hydrogen in the presence of a suitable hydroformylation catalyst under hydroformylation reaction conditions to produce an alcohol having x+1 carbon atoms.

The olefin having x carbon atoms may be any olefinic compound suitable for use in a hydroformylation reaction and includes substituted or unsubstituted, linear or branched, internal or alpha olefins, and mixtures thereof.

Preferably the olefin having x carbon atoms comprises an olefin with a single carbon-carbon double bond. Preferably the starting olefin is an unbranched linear olefin, preferably an alpha olefin. x is preferably an integer of from 2 to 36, more preferably from 4 to 16, especially from 4 to 9.

A suitable feedstock for hydroformylation may contain a single olefin or may be a mixture of olefins.

In one embodiment of the invention, 1-pentene may be converted to 1-hexene. In another embodiment of the invention, 1-heptene may be converted to 1-octene. In another embodiment, a mixture of 1-butene and 1-pentene may be converted into a mixture of 1-pentene and 1-hexene.

In one embodiment of the present invention, a Fischer-Tropsch derived feed stream containing one or more alpha-olefins may be used as a source of the starting olefinic compound.

The process of the present invention may be repeated to obtain chain growth of the formed olefinic compound. For example, the process of the present invention may comprise the additional steps of:

(iii) reacting the olefin having x+1 carbon atoms produced in step (ii) with carbon monoxide and hydrogen in the presence of a hydroformylation catalyst to produce an alcohol having x+2 carbon atoms, and (iv) dehydrating the alcohol produced in step (iii) in the presence of a dehydration catalyst to produce an olefin having x+2 carbon atoms.

By including steps (iii) and (iv) in addition to steps (i) and (ii), 1-butene can be converted to 1-hexene, for example.

Importantly, hydroformylation step (i), and preferably also hydroformylation step (iii) when present, may be carried out in the presence of a hydroformylation catalyst to produce alcohols having a linearity of at least 90%, more preferably at least 92%. Linearity is measured herein using GC analysis.

It is important that the hydroformylation catalyst selected meets these linearity requirements.

The alcohols formed have one more carbon atom than the olefin that is hydroformylated.

It will be appreciated by those skilled in the art that during the hydroformylation step, aldehydes may also be formed in addition to alcohols. Some aldehydes may convert to the corresponding alcohol by means of an in situ hydrogenation reaction. If a significant amount of aldehyde is produced during the hydroformylation step, it is preferred to include a hydrogenation step to convert the aldehyde to an alcohol. Where no significant amount of aldehyde forms during the hydroformylation, a hydrogenation step may not be required.

A preferred hydroformylation catalyst for use herein is a hydroformylation catalyst which is based on:

(a) a source of cobalt, and (b) a ligand selected from:

(i) a ligand of general formula (I):

$$R^1R^2P\text{---}R^3 \tag{I}$$

wherein $R^1$ and $R^2$ are independently a hydrocarbyl group with $C_1$-$C_{12}$ carbon atoms or together with the phosphorus atom P represent an optionally substituted cyclic group with at least 5 ring atoms; and wherein $R^3$ is a monovalent radical of general formula:

$$\text{---}R^4\text{---}C(O)NR^5R^6 \tag{II}$$

wherein $R^4$ is an alkylene group and $R^5$ and $R^6$ independently represent an alkyl, cycloalkyl, aryl, alkaryl or heteroaryl group;

(ii) a ligand of general formula (III):

$$R^1R^2P\text{---}R^4\text{---}C(O)N(R^7)\text{---}R^8\text{---}N(R^7)C(O)\text{---}R^4\text{---}PR^1R^2 \tag{III}$$

wherein $R^1$, $R^2$ and $R^4$ are as defined above, wherein $R^7$ independently represents an alkyl, cycloalkyl, aryl, alkaryl or heteroaryl group, and wherein $R^8$ represents an alkylene, cycloalkylene, arylene or alkarylene group; and (iii) a ligand of general formula (IV):

$$R^1R^2P\text{---}R^4\text{---}C(O)N\text{---}(R^8)_2\text{---}NC(O)\text{---}R^4\text{---}PR^1R^2 \tag{IV}$$

wherein $R^1$, $R^2$, $R^4$ and $R^8$ are as defined above; and mixtures thereof.

Preferably, $R^1$ and $R^2$ together with the phosphorus atom P represent a substituted or non-substituted cyclic group with at least 5 ring atoms, of which one is a phosphorus atom, and preferably with from 6 to 12 ring atoms. The cyclic group may be a monocyclic group, such as for example a substituted or non-substituted phosphacyclohexyl, phosphacycloheptyl or phosphacyclooctyl group, or a polycyclic group. Preferably $R^1$ and $R^2$ together with the phosphorus atom P represent a phospha-bicycloalkyl group with at least 6 ring atoms, such as for example a 7-phosphabicycloheptyl, a 8-phophabicycloheptyl or a 9-phosphabicyclononyl group. Most advantageously $R^1$ and $R^2$ together with the phosphorus atom P represent a substituted or unsubstituted 9-phosphabicyclononyl group. The 9-phosphabicyclononyl group may have several isomeric structures. For the purpose of the invention the [3,3,1] and [4,2,1] isomers are preferred. Suitably $R^1$ and R2 together with the phosphorus atom P represent a substituted or unsubstituted [3,3,1] (i.e. symmetrical) or [4,2,1] (i.e. unsymmetrical) 9-phosphabicyclononyl group, preferably a substituted or unsubstituted [3.3.1] (i.e. symmetrical) 9-phosphabicyclononyl group (also known as S-phobane).

Separation methods for separating symmetrical 9-phosphabicyclononyl groups from unsymmetrical 9-phosphabicyclogroups can be found in the following publications: M. R. Eberhard, E. Carrington-Smith, E. Drent, P. S. Marsh, A. G. Orpen, H. Phetmung and P. G. Pringle, *Adv. Synth. Catal.*, 2005, 347, 1345; and J. H Downing, V. Gee and P. G. Pringle, *Chem. Commun.*, 1997, 1527.

The phosphacycloalkyl ring, or more preferably phosphabicycloalkyl ring, may be substituted with one or more suitable hydrocarbyl groups containing carbon atoms and/or heteroatoms. Suitable substituents include groups containing heteroatoms such as halides, sulphur, phosphorus, oxygen and nitrogen. Examples of such groups include fluoride, chloride, bromide, iodide and groups of the general formula =O, =S, —O—H, —O—$X^3$, —CO—$X^3$, —CO—O—$X^3$, —S—H, —S—$X^3$, —CO—S—$X^3$, —NH$_2$, —NHX$^3$, —NX$^3$X$^4$, —NO$_2$, —CN, —CO—NH$_2$, —CO—NHX$^3$, —CO—NX$^3$X$^4$ and —Cl$_3$, in which $X^3$ and $X^4$, independently, represent alkyl groups having from 1 to 4 carbon atoms like methyl, ethyl, n-propyl, isopropyl, n-butyl, iso-butyl and tert.-butyl. If a phosphabicyclononyl ring is substituted it is preferably substituted with one or more alkyl groups, preferably having from 1 to 10 carbon atoms, more preferably from 1 to 4 carbon atoms. Linear, branched or cyclic alkyl groups may be used. Suitable alkyl groups include, methyl, ethyl, propyl, iso-propyl, butyl and iso-butyl. More suitably methyl groups are used. The substituted phosphabicyclononyl ring may be mono- or poly-substituted and is preferably di-substituted. Most preferably the phosphabicyclononyl ring is substituted with two methyl groups.

Preferably, alkylene group $R^4$ is selected from a $C_1$-$C_{22}$ alkylene group, more preferably a $C_1$-$C_{10}$ alkylene, even more preferably a $C_1$-$C_6$ alkylene group, most preferably methylene, ethylene, propylene or butylene group, and especially an ethylene group.

Preferably $R^5$, $R^6$ and $R^7$ independently represent a $C_1$-$C_{22}$ alkyl, a $C_3$-$C_8$ cycloalkyl, a $C_6$-$C_{14}$ aryl (i.e. an unsaturated aromatic carbocyclic group having from 6 to 14 carbon atoms), a $(C_1$-$C_6)$alk$(C_6$-$C_{14})$aryl group or a heteroaryl group having from 6 to 14 ring atoms (i.e. an unsaturated aromatic carbocyclic group wherein one or more of the ring carbon atoms has been replaced by a heteroatom, such as N, O or S).

More preferably, $R^5$, $R^6$ and $R^7$ independently represent an aryl group, for example, phenyl; or an alkyl group, preferably an alkyl group having from 1 to 22, more preferably from 1 to 10 carbon atoms, even more preferably from 1 to 6 carbon atoms. Examples of alkyl groups that may conveniently be used include methyl, ethyl, propyl, butyl and pentyl groups.

Preferably, $R^8$ represents a $C_6$-$C_{14}$ arylene group, for example, —$C_6H_4$—; or an alkylene group, preferably an alkylene group having from 1 to 22 carbon atoms, more preferably an alkylene group having from 1 to 10 carbon atoms, even more preferably from 1 to 6 carbon atoms. Examples of alkylene groups that may conveniently be used include methylene, ethylene, propylene or butylenes group, most preferably an ethylene group.

Particularly preferred examples of ligands falling within the general formula (I) are 9-dimethylamide propanone-9-phospha-bicyclo-[3.3.1]nonane and 9-dibutylamide propanone-9-phosphabicyclo-[3.3.1]nonane.

An example of a ligand falling under the general formula III is:

$C_8H_{15}P$—$CH_2CH_2$—$C(O)N(CH_3)$—$C_6H_4$—$N(CH_3)$
$C(O)$—$CH_2CH_2$—$PC_8H_{15}$.

An example of a ligand falling under the general formula IV is:

$H_{15}C_8PCH_2CH_2(O)C$—N     N—$C(O)CH_2CH_2PC_8H_{15}$

The ligands of general formula I may be prepared by coupling a suitable $R^1R^2$—P— precursor with a suitable $R^3$ group precursor.

The $R^1R^2$—P— precursor may conveniently be $R^1R^2PH$. Other synthetic $R^1R^2$—P— precursors could be used instead and would be well known to those skilled in the art.

The $R^3$ group precursor may conveniently be an N,N-disubstituted alkenylamide. For example, ligands wherein $R^4$ is an ethylene group and $R^5$ and $R^6$ are alkyl groups may be prepared by reaction of a dialkyl-acrylamide with a $R^1R^2$—P— precursor in the presence of acid, e.g. acetic acid. Other ligands according to the present invention may be prepared by analogous chemistry, as will be understood by those skilled in the art.

The ligands of general formula (III) and (IV) may be prepared by analogous chemistry to that described above in relation to ligands of general formula (I), as will be understood by those skilled in the art.

The cobalt hydroformylation catalyst may be prepared by a diversity of methods well known to those skilled in the art (such as those disclosed in U.S. Pat. Nos. 3,501,515, 3,448, 157, 3,420,898 and 3,440,291. A convenient method is to combine a cobalt salt with the desired ligand, for example, in liquid phase followed by reduction and carbonylation.

The amount of ligand of general formula (I), (III) or (IV) is generally applied in an excess to the amount of cobalt, expressed as moles of ligand per mole of cobalt. Typically the amount of ligand is selected such that per mole of atom of cobalt at least 0.2 moles of ligand are present. For a preferred catalyst system the molar amount of ligand per mole of cobalt is preferably in the range of from 0.2 to 20, more preferably in the range of from 0.4 to 10, especially in the range of from 0.5 to 5.

The source of cobalt is suitably an organic or inorganic cobalt salt. Suitable cobalt salts comprise, for example, cobalt carboxylates such as acetates, octanoates, etc., as well as cobalt salts of mineral acids such as chlorides, fluoride, sulfates, sulfonates, etc. as well as mixtures of one or more of these cobalt salts.

The valence state of the cobalt may be reduced and the cobalt-containing complex formed by heating the solution in an atmosphere of hydrogen and carbon monoxide. The reduction may be performed prior to the use of the catalysts or it may be accomplished simultaneously with the hydroformylation process in the hydroformylation zone.

Alternatively, the catalysts may be prepared from a carbon monoxide complex of cobalt. For example, it is possible to start with dicobalt octacarbonyl and, by mixing this substance with a suitable phosphine ligand, in the reaction medium or in a solvent, the ligand replaces one or more of the carbon monoxide molecules, producing the desired catalyst.

The hydroformylation step (i) is carried out by reacting the olefinic compound with carbon monoxide and hydrogen in the presence of the hydroformylation catalyst and under hydroformylation reaction conditions.

The ratio of catalyst to the olefinic compound to be hydroformylated is generally not critical and may vary widely. It may be varied to achieve a substantially homogeneous reaction mixture. Solvents are therefore not required. However, the use of solvents which are inert, or which do not interfere to any substantial degree with the desired hydroformylation reaction under the conditions employed, may be used. Saturated liquid hydrocarbons, for example, may be used as solvent in the process, as well as alcohols, ethers, acetonitrile, sulfolane, and the like. Molar ratios of catalyst to the olefinic compound in the reaction zone at any given instant between about 1:1000 and about 10:1 are found to be satisfactory; a higher or lower ratio of catalyst to olefinic compound may, however, be used, but in general it will be less than 1:1.

The ratio of hydrogen to carbon monoxide may vary widely. In general, a mole ratio of at least about 1, hydrogen to carbon monoxide, is employed. Suitably ratios of hydrogen to carbon monoxide comprise those within the range of from about 1 to 10. Higher or lower ratios may, however, be employed. The ratio of hydrogen to carbon monoxide employed will be governed to some extent by the nature of the reaction product desired. If conditions are selected that will result primarily in an aldehyde product, only one mole of hydrogen per mole of carbon monoxide enters into reaction with the olefinic compound. When an alcohol is the preferred product of the process of the present invention, two moles of hydrogen and one mole of carbon monoxide react with each mole of olefinic compound. The use of ratios of hydrogen to carbon monoxide which are somewhat lower than those defined by these values are generally preferred.

The process of the present invention may be carried out at various pressures. Consequently, hydroformylation in accordance with the process of the present invention may typically be carried out at pressures below $8 \times 10^6$ Pa, to as low as $1 \times 10^5$ Pa. The process of the present invention is, however, not limited in its applicability to the lower pressures and pressures in the broad range from $1 \times 10^5$ Pa up to about $14 \times 10^6$ Pa and in some cases up to about $20 \times 10^6$ Pa, or even higher, may be employed. Typically, the specific pressure used will be governed to some extent by the specific charge and catalyst employed. In general, pressures in the range of from about $2 \times 10^6$ Pa to $10 \times 10^6$ Pa and particularly in the range of from about $2.7 \times 10^6$ Pa to about $9 \times 10^6$ Pa are preferred.

Temperatures employed in the process of the invention will generally range from about 100° C. to about 300° C. and preferably about 150° C. to about 210° C., a temperature of about 170-180° C. being generally satisfactory. Somewhat higher or lower temperatures may, however, be used within the scope of the invention.

The second step of the process involves the dehydration of the alcohol produced in step (i) (or in step (iii)) in the presence of a dehydration catalyst under dehydration reaction conditions.

Any suitable dehydration process may be used to convert the alcohol produced in step (i) (or in step (iii)) to the corresponding olefin. In cases where the alcohol is an n-alcohol the dehydration process is preferably controlled to produce alpha-olefins.

Preferably the dehydration step is carried out under acidic conditions and a mildly acidic catalyst such as $Al_2O_3$, $SiO_2$, $TiO_2$ or $ZrO_2$ may be employed to afford a dehydration reaction at temperatures from 200 to 450° C., typically from 250 to 350° C. and at pressures of from 0 to 30 barg, typically 0 to 5 barg. The catalyst may comprise a gamma-alumina catalyst or a promoted alumina catalyst e.g. $CaO.Al_2O_3$, $Ca_2O_3.Al_2O_3$. H-type synthetic zeolites may also be used as dehydration catalyst.

The invention will now be further described by means of the following non-limiting examples.

EXAMPLE 1

Hydroformylation of 1-pentene to 1-hexanol

Three types of ligands were used in this experiment:
Ligand 1: A mixture of symmetrical 9-eicosyl-9-phospha-bicyclo-[3.3.1]nonane and non-symmetrical 9-eicosyl-9-phospha-bicyclo[4.2.1] nonane in a ratio of about 55:45
Ligand 2: Symmetrical 9-eicosyl-9-phospha-bicyclo-[3.3.1] nonane (purity of 98%)
Ligand 3: Symmetrical 9-dimethylamide propanone-9-phospha-bicyclo-[3.3.1]nonane (purity of 98%) prepared according to the method below.

Preparation of Ligand 3 (Symmetrical 9-dimethylamide propanone-9-phospha-bicyclo-[3.3.1]nonane)

The preparation of symmetrical 9-dimethylamide propanone-9-phospha-bicyclo-[3.3.1]nonane proceeded as follows:

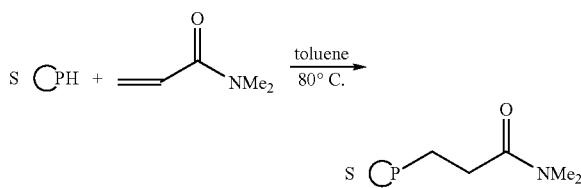

A mixture of 2.12 g S-phobane (symmetrical phobane)(14.9 mmol) and 1.3 ml dimethylacrylamide (12.5 mmol) in 10 ml toluene was heated at 80° C. for 24 hours. The excess phobane and toluene was removed at 50° C. in vacuo yielding 3 g (12 mmol) product. $^{31}$P NMR: −32.2 ppm.

A hydroformylation reaction was carried out at a temperature of 160-171° C., a pressure of 65 bar and a hydrogen/carbon monoxide ratio of 1.4-1.5, employing 2-ethyl hexanol as solvent. The catalyst was prepared by dissolving Co(octoate)2 and one of the phosphine ligands above in 2-ethyl hexanol and injected into a reaction vessel charged with olefin feed, KOH and solvent at the required process (temperature and pressure) conditions. To prevent an initial exotherm and generate a more steady temperature profile during the reaction, the catalyst was injected at a temperature that was roughly 10° C. lower than the target temperature. The progress of the reactions was monitored by analysis of samples taken from the reaction mixture at regular time intervals. To prevent extensive loss of volatile components from the hot samples, these were collected in a small flask charged with solid carbon dioxide. The experimental conditions and end-of-reaction results (t=6-7.5 hours) are given in Table 1 below.

TABLE 1

Experimental Conditions and main results of the hydroformylation reactions

| Ligand | T (° C.) | [Co] (wt %) | Ligand/Co (mol/mol) | KOH/Co (mol/mol) | Conversion (%) | Linearity l/(l + b) | Paraffin (mol %) | Acetal (mol %) | Heavy Ends (mol %) |
|---|---|---|---|---|---|---|---|---|---|
| Ligand 1 | 160 | 0.18 | 1.0 | 0.9 | 98.3 | 93.3 | 6.3 | 9.4 | 4.7 |
| Ligand 3 | 165 | 0.18 | 1.0 | 0.9 | 99.9 | 94.3 | 8.2 | 5.1 | 1.9 |
| Ligand 2 | 170 | 0.18 | 1.0 | 0.9 | 99.8 | 92.1 | 7.0 | 5.6 | 1.7 |
| Ligand 1 | 170 | 0.21 | 2.0 | 0 | 99.9 | 93.3 | 6.5 | 3.1 | 0.1 |
| Ligand 3 | 171 | 0.12 | 1.5 | 0 | 100 | 93.7 | 6.8 | 3.8 | 0.4 |
| Ligand 2 | 170 | 0.10 | 1.5 | 0 | 99.8 | 93.1 | 6.1 | 4.2 | 0.1 |
| Ligand 1 | 170 | 0.20 | 1.3 | 0.5 | 99.8 | 93.0 | 6.0 | 4.2 | 0.6 |
| Ligand 3 | 170 | 0.12 | 1.5 | 0.5 | 99.8 | 94.3 | 5.7 | 2.9 | 1.2 |
| Ligand 2 | 169 | 0.12 | 1.5 | 0.5 | 99.8 | 93.9 | 5.8 | 5.7 | 2.1 |

As can be seen from the results in Table 1, the linearity of the C6 alcohol produced by Ligand 3 is higher than that produced by Ligand 1 or 2.

EXAMPLE 2

Dehydration of 1-hexanol to 1-pentene

A vertical stainless steel tube reactor, 300 mm in length and with internal diameter of 13 mm was sequentially loaded with a 50 mm layer of glass pearls, a layer of about 13 g of star-shaped gamma-alumina catalyst (Engelhard AL 0124 CS*5F 3.5 MM), and another 50 mm layer of glass pearls. The reactor was heated to 340° C. and 1-hexanol vapour was fed into the tube reactor at atmospheric pressure at a WHSV of 1.2 kg hexanol kg$^{-1}$ catalyst hr$^{-1}$. The reaction gas mixture exiting the reactor was passed through a condenser and collected as a two phase mixture, an aqueous and an organic phase. After operating the catalyst bed for 24 hours this way a fresh sample of the organic phase was collected and analyzed by GC. The GC results are given in Table 1. A total of 66.5% of the 1-hexanol was converted, with a selectivity towards hexenes of 50.3 mol %, of which 97.3 wt % was 1-hexene, and towards di-hexylether of 49.7 mol %. In order to improve the conversion and overall selectivity towards hexenes, unconverted hexanol and di-hexylether should be recycled back into the reaction mixture.

EXAMPLE 3

Hydroformylation of 2-butene to 1-pentanol

Hydroformylation of 2-butene (10 mL) was carried out in a 250 mL autoclave at a temperature of 175° C. and total pressure of 80 bar (autoclave was charged with PH2=40 bar and PCO=20 bar at room temperature) employing 2-ethyl-hexanol or methoxybenzene as solvent (30 mL), Co$_2$(CO)$_8$ (85 mg; 0.25 mmol) and a phosphine ligand (1 mmol) (Ligand:Co molar ratio of 2). The reaction time was 10 hours. Two GC runs were used to determine linearity. The results are given in Table 2 below. The ligands used in this experiment were the same as those used in Example 1 above with the addition of Ligand 4 as follows:

Ligand 4: Symmetrical 9-dibutylamide propanone-9-phospha-bicyclo-[3.3.1]nonane

Ligand 4 is prepared using the same method as for ligand 3 except that dibutylacrylamide is used instead of dimethylacrylamide.

TABLE 2

Results from Example 3

| Ligand | Solvent | Linearity L/b (i) | Linearity L/b (ii) | Rate (bar/h) |
|---|---|---|---|---|
| Ligand 3 | 2-EHA | 93.8/6.2 | 92.5/7.5 | 11.5 |
| Ligand 3 | methoxybenzene | 93.6/6.4 | 93.2/6.8 | 10 |
| Ligand 3 | 2-EHA | 93.8/6.2 | 93.5/6.5 | 15.5 |
| Ligand 2 | 2-EHA | 91.7/8.3 | 91.4/8.6 | 15.4 |
| Ligand 4 | 2-EHA | 93.7/6.3 | 93.3/6.7 | 15.4 |

As can be seen from Table 2 the highest regio-selectivity to 1-pentanol was achieved using either Ligand 3 (a phobane-dimethyl-amide) or Ligand 4 (a phobane-dibutyl-amide) as ligand.

The 1-pentanol obtained in this example can be dehydrated in the presence of a suitable dehydration catalyst to give 1-pentene.

What is claimed is:

1. A process for converting an olefin having x carbon atoms into an olefin having x+1 carbon atoms which comprises the steps of:
   (i) reacting an olefin having x carbon atoms with carbon monoxide and hydrogen in the presence of a hydroformylation catalyst to produce an alcohol having x+1 carbon atoms, and
   (ii) dehydrating the alcohol produced in step (i) in the presence of a dehydration catalyst to produce an olefin having x+1 carbon atoms
   characterised in that the hydroformylation catalyst used in step (i) is based on:
   (a) a source of cobalt, and
   (b) a ligand selected from:
   (i) a ligand of general formula (I):

$$R^1R^2P-R^3 \tag{I}$$

wherein $R^1$ and $R^2$ are independently a hydrocarbyl group with $C_1$-$C_{12}$ carbon atoms or together with the phosphorus atom P represent an optionally substituted cyclic group with at least 5 ring atoms;
   and wherein $R^3$ is a monovalent radical of general formula:

$$-R^4-C(O)NR^5R^6 \tag{II}$$

wherein $R^4$ is an alkylene group and $R^5$ and $R^6$ independently represent an alkyl, cycloalkyl, aryl, alkaryl or heteroaryl group;
   (ii) a ligand of general formula (III):

$$R^1R^2P-R^4-C(O)N(R^7)-R^8-N(R^7)C(O)-R^4-PR^1R^2 \tag{III}$$

wherein $R^1$, $R^2$ and $R^4$ are as defined above, wherein $R^7$ independently represents an alkyl, cycloalkyl, aryl, alkaryl or heteroaryl group, and wherein $R^8$ represents an alkylene, cycloalkylene, arylene or alkarylene group; and
   (iii) a ligand of general formula (IV):

$$R^1R^2P-R^4-C(O)N-(R^8)_2-NC(O)-R^4-PR^1R^2 \tag{IV}$$

wherein $R^1$, $R^2$, $R^4$ and $R^8$ are as defined above;
   and mixtures thereof.

2. The process of claim 1 wherein $R^1$ and $R^2$ together with the phosphorus atom P form an optionally substituted cyclic group having at least 5 ring atoms.

3. The process of claim 1 wherein $R^5$ and $R^6$ independently represent a $C_1$-$C_6$ alkyl group.

4. The process of claim 1 wherein the olefin having x carbon atoms is a linear alpha olefin.

5. The process of claim 1 wherein x is an integer of from 4 to 36.

6. The process of claim 1 wherein 1-pentene is converted to 1-hexene.

7. The process of claim 1 wherein 1-heptene is converted to 1-octene.

8. The process of claim 1 additionally comprising the steps of:
   (iii) reacting the olefin having x+1 carbon atoms produced in step (ii) with carbon monoxide and hydrogen in the presence of a hydroformylation catalyst to produce an alcohol having x+2 carbon atoms, and
   (iv) dehydrating the alcohol produced in step (iii) in the presence of a dehydration catalyst to produce an olefin having x+2 carbon atoms.

9. The process of claim 8 wherein hydroformylation step (iii) is carried out in the presence of a hydroformylation catalyst which is based on:

(a) a source of cobalt, and
(b) a ligand selected from:
(i) a ligand of general formula (I):

$$R^1R^2P-R^3 \qquad (I)$$

wherein $R^1$ and $R^2$ are independently a hydrocarbyl group with $C_1$-$C_{12}$ carbon atoms or together with the phosphorus atom P represent an optionally substituted cyclic group with at least 5 ring atoms;

and wherein $R^3$ is a monovalent radical of general formula:

$$-R^4-C(O)NR^5R^6 \qquad (II)$$

wherein $R^4$ is an alkylene group and $R^5$ and $R^6$ independently represent an alkyl, cycloalkyl, aryl, alkaryl or heteroaryl group;

(ii) a ligand of general formula (III):

$$R^1R^2P-R^4-C(O)N(R^7)-R^8-N(R^7)C(O)-R^4-PR^1R^2 \qquad (III)$$

wherein $R^1$, $R^2$ and $R^4$ are as defined above, wherein $R^7$ independently represents an alkyl, cycloalkyl, aryl, alkaryl or heteroaryl group, and wherein $R^8$ represents an alkylene, cycloalkylene, arylene or alkarylene group; and (iii) a ligand of general formula (IV):

$$R^1R^2P-R^4-C(O)N-(R^8)_2-NC(O)-R^4-PR^1R^2 \qquad (IV)$$

wherein $R^1$, $R^2$, $R^4$ and $R^8$ are as defined above; and mixtures thereof.

10. The process of claim 8 wherein 1-butene is converted to 1-hexene.

* * * * *